US008256858B2

(12) United States Patent
Oshima et al.

(10) Patent No.: US 8,256,858 B2
(45) Date of Patent: Sep. 4, 2012

(54) LIQUID EJECTION DEVICE AND LIQUID EJECTION PRINTER

(75) Inventors: Atsushi Oshima, Shiojiri (JP); Kunio Tabata, Shiojiri (JP); Shinichi Miyazaki, Suwa (JP); Hiroyuki Yoshino, Matsumoto (JP); Noritaka Ide, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 124 days.

(21) Appl. No.: 12/914,377

(22) Filed: Oct. 28, 2010

(65) Prior Publication Data
US 2011/0109674 A1 May 12, 2011

(30) Foreign Application Priority Data

Nov. 10, 2009 (JP) ................................ 2009-257375

(51) Int. Cl.
*B41J 29/38* (2006.01)
(52) U.S. Cl. .................... 347/10; 347/5; 347/9
(58) Field of Classification Search .................. 347/5, 9, 347/10, 14, 68, 70–72, 57–59
See application file for complete search history.

(56) References Cited

U.S. PATENT DOCUMENTS

| 7,244,007 | B2 * | 7/2007 | Ishizaki ............................ 347/5 |
|---|---|---|---|
| 2007/0079710 | A1 | 4/2007 | Ishizaki |
| 2008/0018687 | A1 * | 1/2008 | Tabata et al. .................... 347/11 |
| 2008/0218545 | A1 | 9/2008 | Oshima et al. |
| 2009/0066739 | A1 | 3/2009 | Tabata et al. |
| 2009/0140780 | A1 | 6/2009 | Miyazaki et al. |
| 2009/0160891 | A1 | 6/2009 | Ishizaki |

FOREIGN PATENT DOCUMENTS

| JP | 11-204850 | 7/1999 |
|---|---|---|
| JP | 2007-096364 | 4/2007 |
| JP | 2008-087467 | 4/2008 |
| JP | 2009-131990 | 6/2009 |
| JP | 2009-153272 | 7/2009 |
| WO | 2007/083669 A1 | 7/2007 |

* cited by examiner

*Primary Examiner* — Juanita D Jackson
(74) *Attorney, Agent, or Firm* — Maschoff Gilmore & Israelsen

(57) ABSTRACT

A liquid ejection device includes: a drive waveform generator generating a drive waveform signal; a modulator performing pulse modulation on a signal from the drive waveform generator to provide a modulated signal; a digital power amplifier performing power amplification on the modulated signal to provide an amplified digital signal; a Lowpass Filter smoothing the amplified digital signal to provide a drive signal of an actuator; a compensator advancing the phase of the drive signal to provide a negative feedback signal; and a subtractor providing a differential signal between the drive waveform signal and the negative feedback signal as an input signal to the modulator.

3 Claims, 9 Drawing Sheets

LIQUID EJECTION DEVICE AND LIQUID EJECTION PRINTER

BACKGROUND

1. Technical Field

The present invention relates to a liquid ejection device which performs power amplification on a drive signal to an actuator ejecting a liquid, and is suitable for a liquid ejection printer which prints characters, images, etc. by ejecting a minute liquid droplet out of a nozzle of a liquid ejection head and forming fine particles (dots) on a printing medium.

2. Related Art

In a liquid ejection printer, an actuator such as a piezoelectric element is provided and a predetermined drive signal has to be applied to this actuator to eject a liquid out of a nozzle of a liquid ejection head. Since this drive signal has a relatively high voltage, it is necessary to perform power amplification on a drive waveform signal serving as a reference of the drive signal by using a power amplifier. Therefore, in JP-A-11-204850, a digital power amplifier which has an extremely small power loss compared to an analog power amplifier and can be made compact is used, pulse modulation is performed on a drive waveform signal by a modulator to obtain a modulated signal, power amplification is performed on the modulated signal by the digital power amplifier to obtain an amplified digital signal, and the amplified digital signal is smoothed by a Lowpass Filter to obtain a drive signal.

However, when the actuator is a capacitive load such as a piezoelectric element, the Lowpass Filter needs a damping resistor because of the absence of a resistance component, resulting in a large power loss due to this damping resistor. That is, as is well known, when a Lowpass Filter is formed of a coil and a capacitor, there is a resonance frequency represented by the inductance L of the coil and the capacity C of the capacitor, and the presence of this resonance frequency makes it possible to store power and attenuate voltage fluctuations corresponding to the modulation frequency. However, resonance sometimes occurs due to the resonance frequency. When a resistance component is present in a circuit, the resonance is suppressed (attenuated) by the resistance component; however, since a capacitive load such as a piezoelectric element has no or an extremely small resistance component, the resonance is not suppressed (attenuated) and remains. To suppress (attenuate) the remaining resonance, a circuit has to be provided with a resistor called a damping resistor for suppressing (attenuating) the resonance, and power is consumed when the damping resistor suppresses (attenuates) the resonance.

SUMMARY

An advantage of some aspects of the invention is to provide a liquid ejection device and a liquid ejection printer that can reduce a power loss due to a damping resistor.

A liquid ejection device according to an aspect of the invention includes a drive waveform generator generating a drive waveform signal, a modulator performing pulse modulation on a signal from the drive waveform generator to provide a modulated signal, a digital power amplifier performing power amplification on the modulated signal to provide an amplified digital signal, a Lowpass Filter smoothing the amplified digital signal to provide a drive signal of an actuator, a compensator advancing the phase of the drive signal to provide a negative feedback signal, and a subtractor providing a differential signal between the drive waveform signal and the negative feedback signal as an input signal to the modulator.

According to this liquid ejection device, a resonance characteristic produced when no damping resistor is used in the Lowpass Filter can be compensated for by a negative feedback signal. This eliminates the need for a damping resistor, and makes it possible to reduce power loss. That is, since pulse modulation is performed on a differential signal between the drive waveform signal and the negative feedback signal by the modulator, when, for example, resonance is produced in the drive signal, the differential signal corresponds to an inversion signal of the resonance produced in the drive signal. Thus, by performing pulse modulation on the differential signal and performing power amplification thereon and then adding the resultant signal to the drive signal, it is possible to obtain the original drive signal.

The liquid ejection device may include an inverse filter provided between the drive waveform generator and the subtractor and correcting the frequency characteristic of a closed loop formed of the modulator, the digital power amplifier, the Lowpass Filter, the capacitance of the actuator, and the compensator so as to be constant in a predetermined frequency domain.

According to this liquid ejection device, by correcting the frequency characteristic of a closed loop formed of the modulator, the digital power amplifier, the Lowpass Filter, the capacitance of the actuator, and the compensator, the frequency characteristic which changes with the number of actuators which are driven, so as to be constant in a predetermined frequency domain by the inverse filter, for example, it is possible to ensure the accuracy of the drive signal.

A liquid ejection printer according to another aspect of the invention uses the liquid ejection device described above.

BRIEF DESCRIPTION OF THE DRAWINGS

The invention will be described with reference to the accompanying drawings, wherein like numbers reference like elements.

DESCRIPTION OF EXEMPLARY EMBODIMENTS

As a first embodiment of a liquid ejection device of the invention, a liquid ejection device used in a liquid ejection printer will be described.

Figure 1:
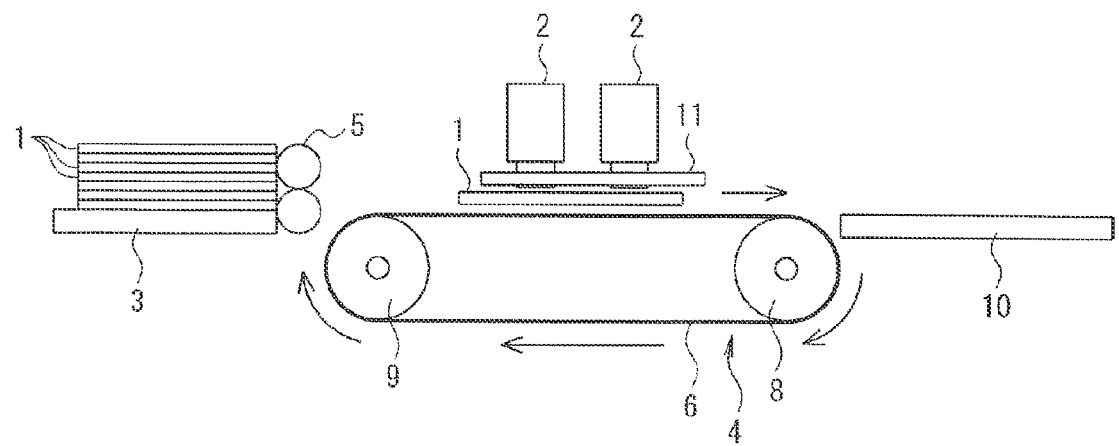
FIG. 1 is a schematic configuration front view showing a first embodiment of a liquid ejection printer using a liquid ejection device of the invention.

FIG. 1 is a schematic configuration diagram of a liquid ejection printer of the first embodiment. This liquid ejection printer is a line head printer in which a printing medium 1 is conveyed from left to right in an arrow direction in FIG. 1 and printing is performed thereon in a printing region located along a path on which the printing medium 1 is being conveyed.

Figure 2:
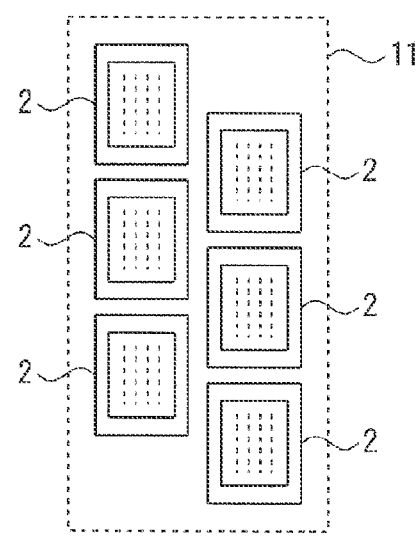
FIG. 2 is a plan view of an area near a liquid ejection head used in the liquid ejection printer of FIG. 1.

In FIG. 1, a plurality of liquid ejection heads 2 are provided above a conveying line of the printing medium 1. The liquid ejection heads 2 are disposed so that they form two lines in a printing medium conveying direction and are arranged next to one another in a direction intersecting the printing medium conveying direction, and are fixed to a head fixing plate 11. On the lowermost face of each liquid ejection head 2, a large number of nozzles are formed, and this face is called a nozzle face. As shown in FIG. 2, the nozzles are disposed, according to a color of a liquid to be ejected, in a line in a direction intersecting the printing medium conveying direction. The line is called a nozzle line, and the line direction is called a nozzle line direction. The nozzle lines of all the liquid ejection heads 2 disposed in a direction intersecting the printing medium conveying direction form a line head running along the width in a direction intersecting the direction in which the printing medium 1 is conveyed. When the printing medium 1 passes under the nozzle faces of these liquid ejection heads 2, a liquid is ejected from a large number of nozzles formed on the nozzle faces, and printing is performed.

To the liquid ejection heads 2, ink liquids of four colors: yellow (Y), magenta (M), cyan (C), and black (K), for example, are supplied from unillustrated liquid tanks through liquid supplying tubes. The required amount of liquid is ejected at a proper area simultaneously out of the nozzles formed in the liquid ejection heads 2, whereby fine dots are formed on the printing medium 1. A liquid of each color is ejected, whereby printing can be performed by passing the printing medium 1 under the nozzle faces once, the printing medium 1 being conveyed by a conveying section 4.

Methods for ejecting the liquid out of the nozzles of the liquid ejection heads 2 include an electrostatic system, a piezo system, a film boiling liquid ejection system, etc.; in this embodiment, the piezo system is used. The piezo system is a system in which, when a drive signal is fed to a piezoelectric element which is an actuator, a vibrating plate in a cavity is displaced, causing a pressure change inside the cavity, and the liquid is ejected out of the nozzle due to the pressure change. By adjusting a peak value or a voltage increase and decrease gradient of the drive signal, it is possible to adjust the ejection amount of the liquid. The invention can also be applied similarly to a liquid ejection method other than the piezo system.

The conveying section 4 for conveying the printing medium 1 in a conveying direction is provided under the liquid ejection heads 2. The conveying section 4 is formed by winding a conveying belt 6 around a driving roller 8 and a driven roller 9, and an unillustrated electric motor is connected to the driving roller 8. Inside the conveying belt 6, an unillustrated sticking apparatus for making the printing medium 1 stuck to the surface of the conveying belt 6 is provided. As the sticking apparatus, for example, an air sucking apparatus which makes the printing medium 1 stuck to the conveying belt 6 by negative pressure or an electrostatic sticking apparatus which makes the printing medium 1 stuck to the conveying belt 6 by electrostatic force is used. Therefore, when only one sheet of printing medium 1 is fed on the conveying belt 6 by a paper feed roller 5 from a paper feed section 3 and the driving roller 8 is driven and rotated by the electric motor, the conveying belt 6 is rotated in the printing medium conveying direction, and the printing medium 1 is conveyed while being stuck to the conveying belt 6 by the sticking apparatus. Printing is performed by ejecting the liquid from the liquid ejection heads 2 while the printing medium 1 is being conveyed. The printing medium 1 on which printing has been performed is ejected into a paper ejection section 10 located downstream in the conveying direction. A printing reference signal output apparatus formed of a linear encoder, for example, is attached to the conveying belt 6. Exploiting the fact that the conveying belt 6 and the printing medium 1 which is conveyed while being stuck to the conveying belt 6 are moved in synchronization with each other, the printing reference signal output apparatus outputs a pulse signal corresponding to a printing resolution which is required with the movement of the conveying belt 6 after the printing medium 1 has passed a predetermined position on a conveying path, and outputs a drive signal according to the pulse signal from a drive circuit, which will be described later, to an actuator 22, thereby ejecting a liquid of a predetermined color at a predetermined position on the printing medium 1 and forming a predetermined image on the printing medium 1 by the dots of the liquid.

Figure 3:
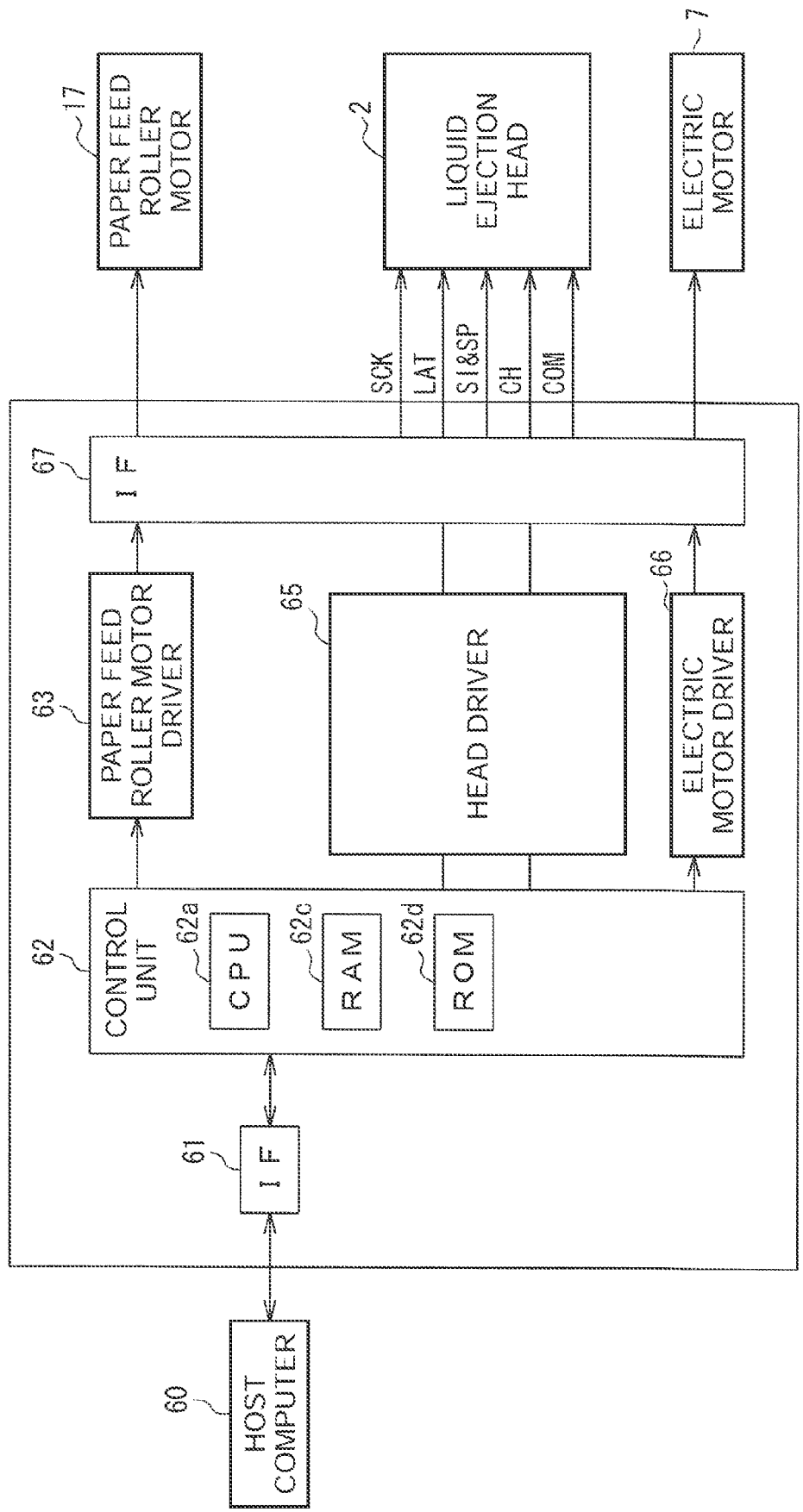
FIG. 3 is a block diagram of a control device of the liquid ejection printer of FIG. 1.

In the liquid ejection printer using the liquid ejection device of this embodiment, a control device for controlling the liquid ejection printer is provided. As shown in FIG. 3, this control device includes an input interface 61 for reading the printing data input from a host computer 60, a control unit 62 which is formed of a microcomputer performing computing such as print processing based on the printing data input from the input interface 61, a paper feed roller motor driver 63 controlling the driving of a paper feed roller motor 17 connected to the paper feed roller 5, a head driver 65 controlling the driving of the liquid ejection head 2, an electric motor driver 66 controlling the driving of an electric motor 7 connected to the driving roller 8, and an interface 67 connecting the paper feed roller motor driver 63, the head driver 65, and the electric motor driver 66 with the paper feed roller motor 17, the liquid ejection head 2, and the electric motor 7.

The control unit 62 includes a CPU (central processing unit) 62a performing various types of processing such as print processing, RAM (random access memory) 62c which temporarily stores printing data input via the input interface 61 or various data used when, for example, print processing is performed by using the printing data, or temporarily expands a program product for print processing etc., and ROM (read-only memory) 62d formed of nonvolatile semiconductor memory storing a control program product etc. executed by the CPU 62a. When the control unit 62 obtains printing data (image data) from the host computer 60 via the input interface 61, the CPU 62a executes predetermined processing on this printing data, calculates nozzle selection data (drive pulse selection data) on a nozzle out of which the liquid is ejected or the amount of liquid to be ejected, and outputs a drive signal and a control signal to the paper feed roller motor driver 63, the head driver 65, and the electric motor driver 66 based on the printing data, the drive pulse selection data, and the input data from various sensors. The paper feed roller motor 17, the electric motor 7, the actuator 22 in the liquid ejection head 2, and the like, are individually activated by the drive signal and the control signal, whereby the printing medium 1 is fed, conveyed, and ejected and print processing is performed on the printing medium 1. The component elements in the control unit 62 are electrically connected via an unillustrated bus.

Figure 4:
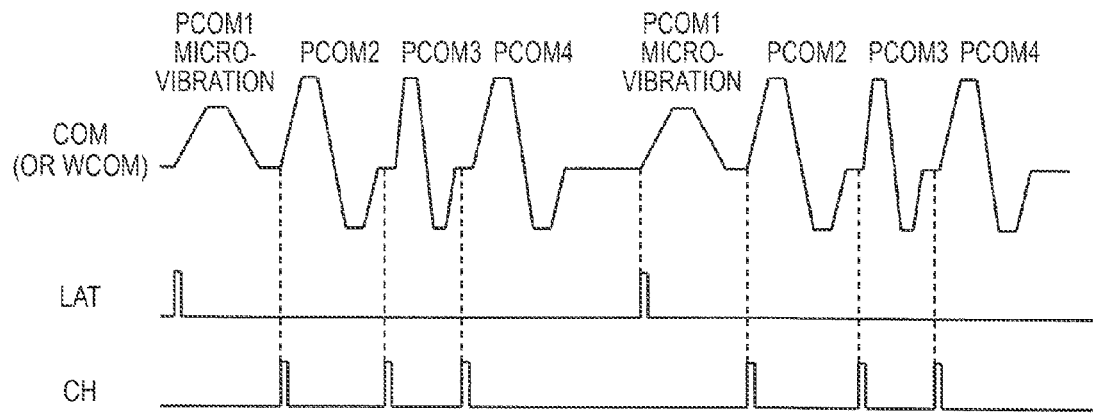
FIG. 4 is an explanatory diagram of a drive signal driving an actuator in each liquid ejection head.

In FIG. 4, an example of a drive signal COM which is fed to the liquid ejection head 2 from the control device of the liquid ejection printer using the liquid ejection device of this embodiment and drives the actuator 22 formed of a piezoelectric element is shown. In this embodiment, the drive signal COM is assumed to be a signal having a voltage changing with an intermediate voltage at the center. The drive signal COM is a signal obtained as drive pulses PCOM connected in chronological order, the drive pulses PCOM which are unit drive signals for driving the actuator 22 to eject the liquid. A rising edge of the drive pulse PCOM corresponds to a stage at which the liquid is drawn (for a face to which the liquid is ejected, it can be said that the meniscus is drawn) by increasing the volume of the cavity (the pressure chamber) communicating with the nozzle. A trailing edge of the drive pulse PCOM corresponds to a stage at which the liquid is pushed out (for a face to which the liquid is ejected, it can be said that the meniscus is pushed out) by reducing the volume of the cavity, and the liquid is ejected out of the nozzle as a result of the liquid being pushed out.

By variously changing a voltage increase and decrease gradient or a peak value of the drive pulse PCOM formed of a voltage trapezoidal wave, it is possible to change the amount of drawn liquid, the rate at which the liquid is drawn, the amount of liquid pushed out, and the rate at which the liquid is pushed out. This makes it possible to change the amount of liquid to be ejected and obtain dots of different sizes. Therefore, even when a plurality of drive pulses PCOM are connected in chronological order, the liquid is ejected by selecting a single drive pulse PCOM from among the drive pulses PCOM and feeding the drive pulse PCOM to the actuator 22 or the liquid is ejected multiple times by selecting a plurality of drive pulses PCOM from among the drive pulses PCOM and feeding the drive pulses PCOM to the actuator 22, whereby it is possible to obtain dots of various sizes. That is, putting the liquid in the same position multiple times before the liquid is dried out is substantially identical to ejecting a large droplet of liquid. Thus, it is possible to increase the size of a dot. By combining the techniques in this way, it is possible to realize multistep gradation. A drive pulse PCOM 1 on the far left in FIG. 4 only draws the liquid and does not pushes out the liquid. This is called micro-vibration, and is used for suppressing and preventing the thickening of the nozzle without ejecting the liquid.

To the liquid ejection head 2, in addition to the drive signal COM, drive pulse selection data SI&SP selecting a nozzle out of which the liquid is ejected based on the printing data and determining connecting timing with which the actuator 22 such as a piezoelectric element is connected to the drive signal COM, a latch signal LAT and a channel signal CH which connect the drive signal COM and the actuator 22 of the liquid ejection head 2 based on the drive pulse selection data SI&SP after the nozzle selection data is input to all the nozzles, and a clock signal SCK for transmitting the drive pulse selection data SI&SP to the liquid ejection head 2 as a serial signal are input as a control signal from the control device of FIG. 3. Hereinafter, a minimum unit of the drive signal driving the actuator 22 is referred to as a drive pulse PCOM, and the whole signal obtained as the drive pulses PCOM connected in chronological order is referred to as a drive signal COM. That is, with the latch signal LAT, a series of drive signals COM is started to be output, and the drive pulse PCOM is output with each channel signal CH. Of the drive pulse selection data SI&SP, the drive pulse selection identification data SI is 2-bit data indicating which drive pulse PCOM is selected from among the above-described drive pulses PCOM, and SP is 16-bit selection switch control data for performing on/off control of a selection switch, which will be described later, in accordance with the timing of the selected drive pulse PCOM.

Figure 5:
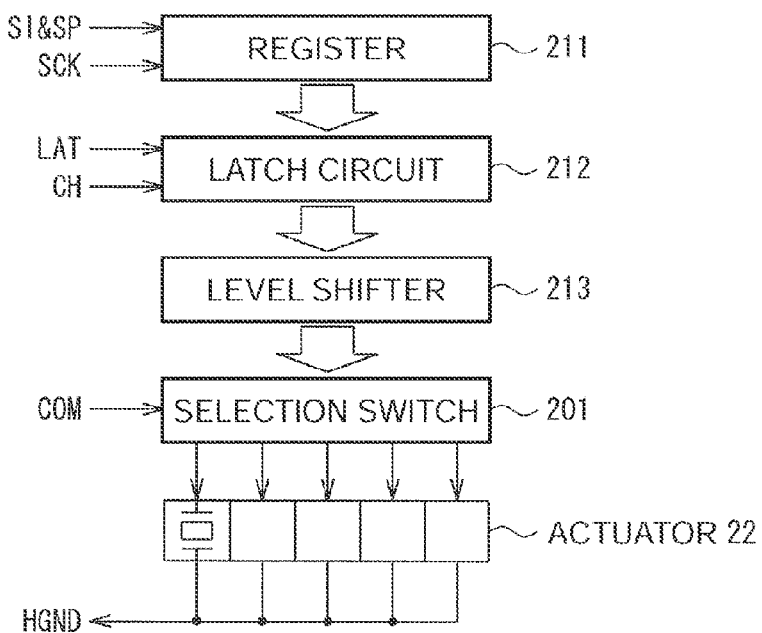
FIG. 5 is a block diagram of a switching controller.

In FIG. 5, a specific configuration of a switching controller configured in the liquid ejection head 2 for feeding the drive signal COM (the drive pulse PCOM) to the actuator 22 is shown. The switching controller includes a register 211 storing the drive pulse selection data SI&SP for specifying the actuator 22 such as a piezoelectric element corresponding to the nozzle out of which the liquid is ejected, a latch circuit 212 temporarily storing the data of the register 211, and a level shifter 213 connecting the drive signal COM (the drive pulse PCOM) to the actuator 22 such as a piezoelectric element by performing level conversion of the output of the latch circuit 212 and feeding the output to the selection switch 201.

To the register 211, the drive pulse selection data SI&SP is input according to the input pulse of the clock signal SCK, and the selection switch control data SP is stored in a predetermined address. The latch circuit 212 latches the output signals of the register 211 by the input latch signal LAT after the selection switch control data SP of all the actuators is stored in the register 211. The signal stored in the latch circuit 212 is converted by the level shifter 213 into a voltage level which can turn on/off the selection switch 201 in the following stage. This is because the drive signal COM (the drive pulse PCOM) is a voltage higher than the output voltage of the latch circuit 212 and the operating voltage range of the selection switch 201 is set at a high level accordingly. Therefore, the actuator 22 such as a piezoelectric element with the selection switch 201 which is closed by the level shifter 213 is connected to the drive signal COM (the drive pulse PCOM) with the connection timing of the drive pulse selection data SI&SP (the selection switch control data SP). After the drive pulse selection data SI&SP (the selection switch control data SP) of the register 211 is stored in the latch circuit 212, the next printing information is input to the register 211, and the stored data of the latch circuit 212 is sequentially updated according to the timing with which the liquid is ejected. A sign HGND in the drawing denotes a ground end of the actuator 22 such as a piezoelectric element. Thanks to the selection switch 201, even after the actuator 22 such as a piezoelectric element is disconnected from the drive signal COM (the drive pulse PCOM), the input voltage of the actuator 22 is maintained at a voltage just before the disconnection.

Figure 6:
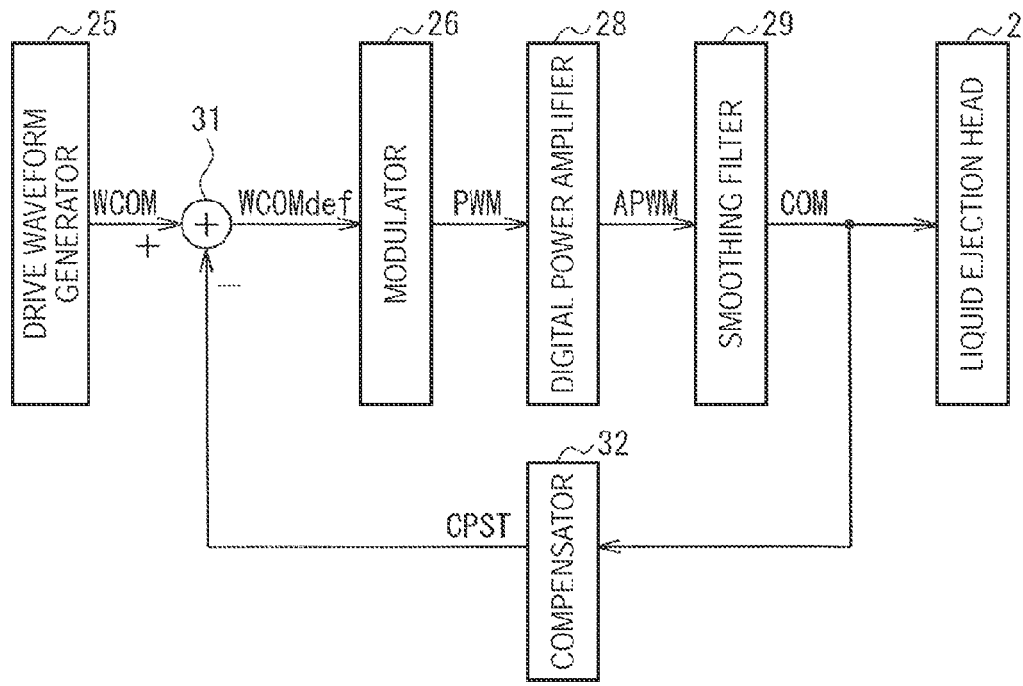
FIG. 6 is a block diagram showing an example of a drive circuit of the actuator.

In FIG. 6, a schematic configuration of a drive circuit of the actuator 22 is shown. This actuator drive circuit is configured in the control unit 62 and the head driver 65 which are provided in the control circuit. The drive circuit of this embodiment includes a drive waveform generator 25 generating a drive waveform signal WCOM from which a drive signal COM (a drive pulse PCOM) is generated, that is, the drive waveform signal WCOM which serves as a reference of a signal controlling the driving of the actuator 22, an adder-subtractor 31 serving as a subtractor outputting a difference between the drive waveform signal WCOM generated by the drive waveform generator 25 and a negative feedback signal from a compensator, which will be described later, specifically, a differential signal WCOMdef obtained by subtracting a negative feedback signal from the drive waveform signal WCOM, a modulator 26 outputting a modulated signal PWM by performing pulse modulation on the differential signal WCOMdef from the adder-subtractor 31, a digital power amplifier 28 performing power amplification on the modulated signal PWM from the modulator 26 and outputting an amplified digital signal APWM, a Lowpass Filter 29 smoothing the amplified digital signal APWM from the digital power amplifier 28 and outputting the resultant signal as a drive signal COM, and a compensator 32 advancing the phase of the drive signal COM and outputting a negative feedback signal CPST.

The drive waveform generator 25 holds and outputs the drive waveform data DWCOM read from the waveform memory for a predetermined sampling period.

Figure 7:
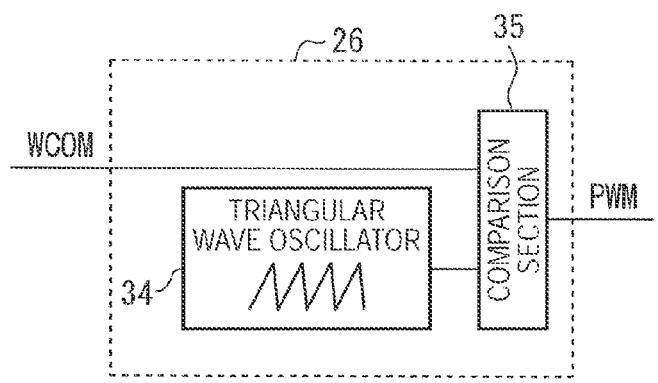
FIG. 7 is a block diagram of a modulator of FIG. 6.

As the modulator 26 performing pulse modulation on the drive waveform signal WCOM, as shown in FIG. 7, a well-known pulse width modulation (PWM) circuit is used. The pulse width modulation circuit includes a triangular wave oscillator 34 outputting a triangular wave signal having a predetermined frequency and a comparison section 35 comparing the triangular wave signal with the drive waveform signal WCOM and outputting a modulated signal PWM with pulse duty cycle in which on duty cycle comes when the drive waveform signal WCOM is greater than the triangular wave signal, for example.

The drive waveform generator 25, the adder-subtractor 31 which is a subtractor, and the modulator 26 can also be configured by computing performed by a program product. As the modulator 26, a well-known pulse modulation circuit such as a pulse density modulation (PDM) circuit can be used instead.

Figure 8:
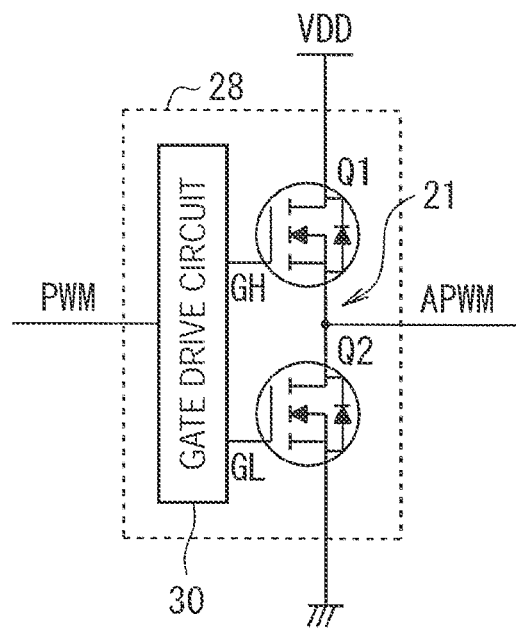
FIG. 8 is a block diagram of a digital power amplifier of FIG. 6.

As shown in FIG. 8, the digital power amplifier 28 includes a half-bridge output stage 21 formed of a high-side switching element Q1 and a low-side switching element Q2 for substantially amplifying power and a gate drive circuit 30 for adjusting gate-source signals GH and GL of the high-side switching element Q1 and the low-side switching element Q2 based on the modulated signal PWM from the modulator 26. In the digital power amplifier 28, when the modulated signal is at high level, the gate-source signal GH of the high-side switching element Q1 becomes high level, and the gate-source signal GL of the low-side switching element Q2 becomes low level. Therefore, the high-side switching element Q1 is brought into an on state, and the low-side switching element Q2 is brought into an off state. As a result, the output voltage Va of the half-bridge output stage 21 becomes a supply voltage VDD. On the other hand, when the modulated signal is at low level, the gate-source signal GH of the high-side switching element Q1 becomes low level, and the gate-source signal GL of the low-side switching element Q2 becomes high level. Therefore, the high-side switching element Q1 is brought into an off state, and the low-side switching element Q2 is brought into an on state. As a result, the output voltage Va of the half-bridge output stage 21 becomes 0.

When the high-side switching element Q1 and the low-side switching element Q2 are digitally driven in this way, a current flows through the switching element in an on state, but the drain-source resistance value is extremely small and therefore losses hardly occur. Since no current flows through the switching element in an off state, no losses occur. Therefore, the loss itself of the digital power amplifier 28 is extremely small, and a switching element such as a small MOS FET can be used.

Figure 9:
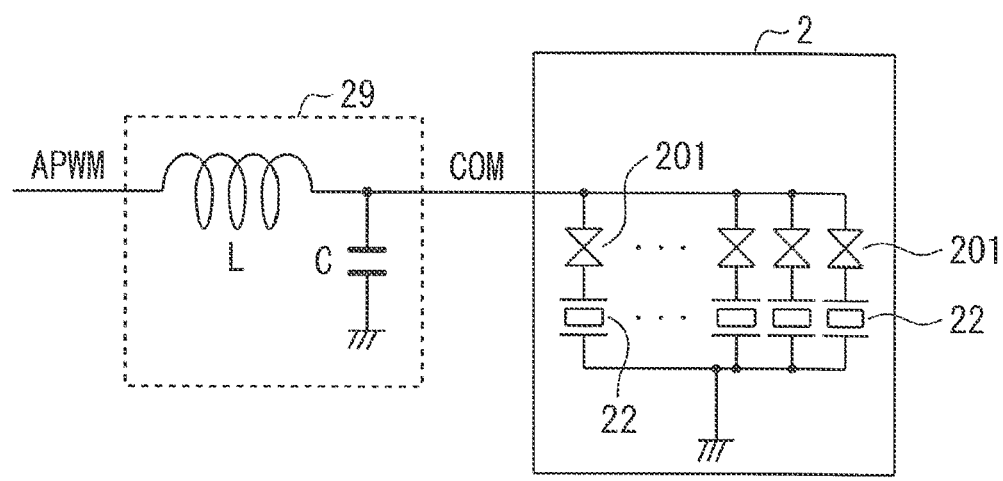
FIG. 9 is a block diagram of a Lowpass Filter of FIG. 6.

As shown in FIG. 9, as the Lowpass Filter 29, a secondary low-pass filter formed of one capacitor C and one coil L is used. A modulation frequency generated in the modulator 26, that is, a frequency component of pulse modulation is attenuated and removed by using this Lowpass Filter 29, and a drive signal COM is output to the actuator 22 via the selection switch 201.

Figure 10:
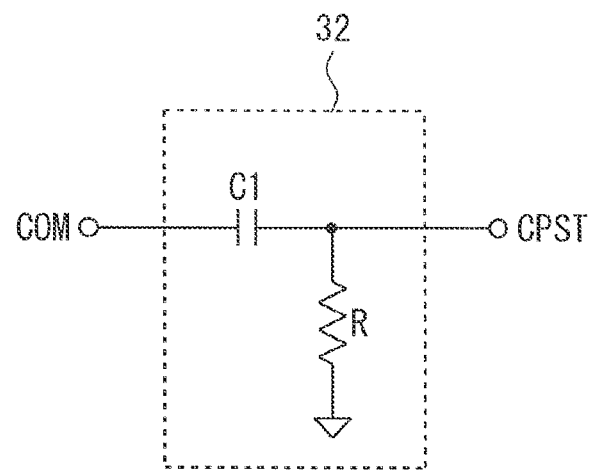
FIG. 10 is a block diagram of a compensator of FIG. 6.

As shown in FIG. 10, the compensator 32 is formed of a high-pass filter which is formed of one capacitor C1 and one resistor R and outputs a negative feedback signal CPST by advancing the phase of a drive signal COM. By making the resistor R of the compensator 32 have a large resistance value, it is possible to reduce the value of a current flowing through the resistor R and reduce power loss.

Figure 11:
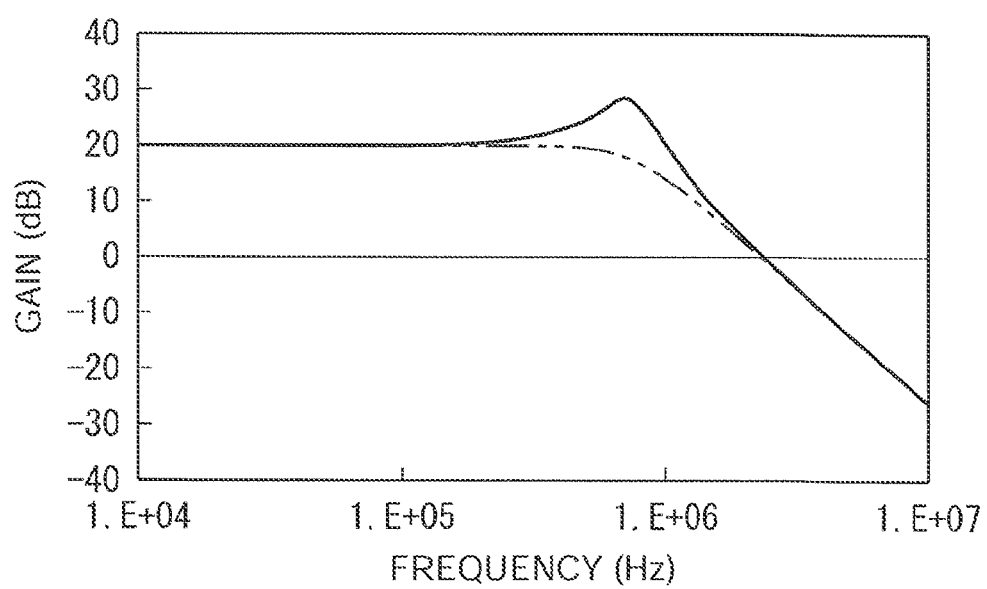
FIG. 11 is an explanatory diagram of the frequency characteristic of the Lowpass Filter of FIG. 9.

As shown by the solid line in FIG. 11, the frequency characteristic of the Lowpass Filter 29 of the first embodiment, the Lowpass Filter 29 with no damping resistor, shows resonance near an attenuation start frequency of the low-pass filter. Such gain fluctuations are not desirable, and a frequency characteristic shown by the chain double-dashed line in FIG. 11, the frequency characteristic in which a gain is constant until an attenuation start frequency, is ideal. In the field of audio, an ideal frequency characteristic can be sometimes obtained without adding a damping resistor due to the influence of a floating resistor or the like. However, since the actuator of the first embodiment, the actuator 22 formed of a capacitive load such as a piezoelectric element, has no resistance component, a damping resistor is indispensable to achieve the frequency characteristic shown by the chain double-dashed line with the Lowpass Filter 29 itself, and this damping resistor results in an increase in power loss.

Figure 12:
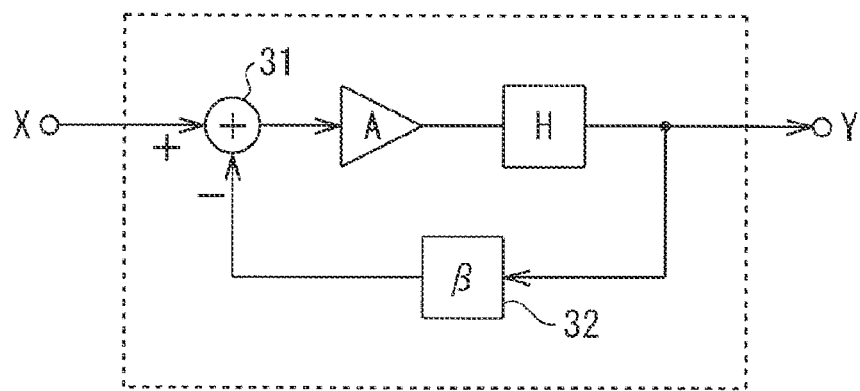
FIG. 12 is an explanatory diagram of a closed loop formed of a modulator, a digital power amplifier, a Lowpass Filter, an actuator, and a compensator.
Figure 13:
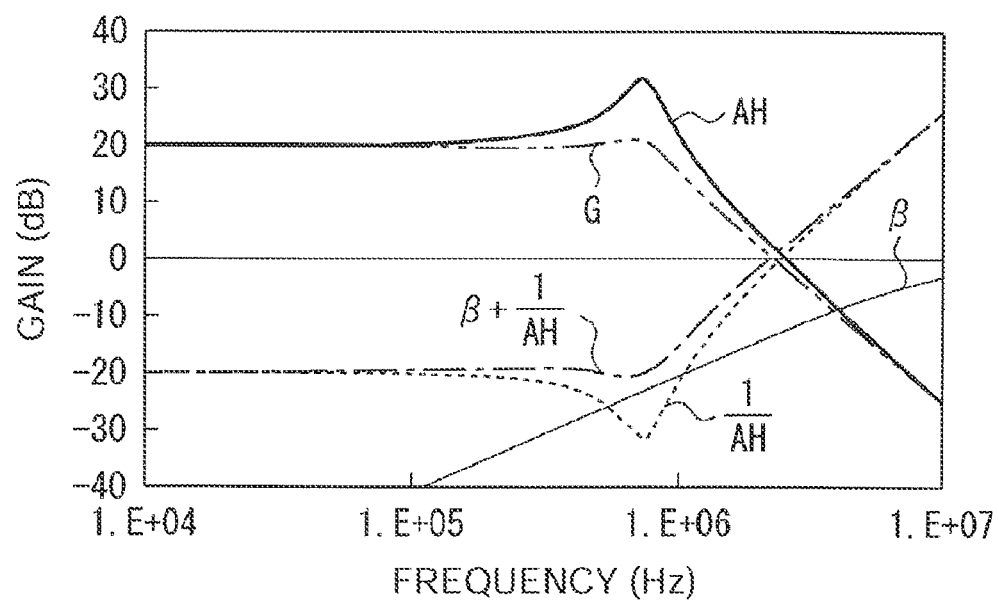
FIG. 13 is an explanatory diagram of a correction of the frequency characteristic of the closed loop, the correction made by the compensator.
Figure 14:
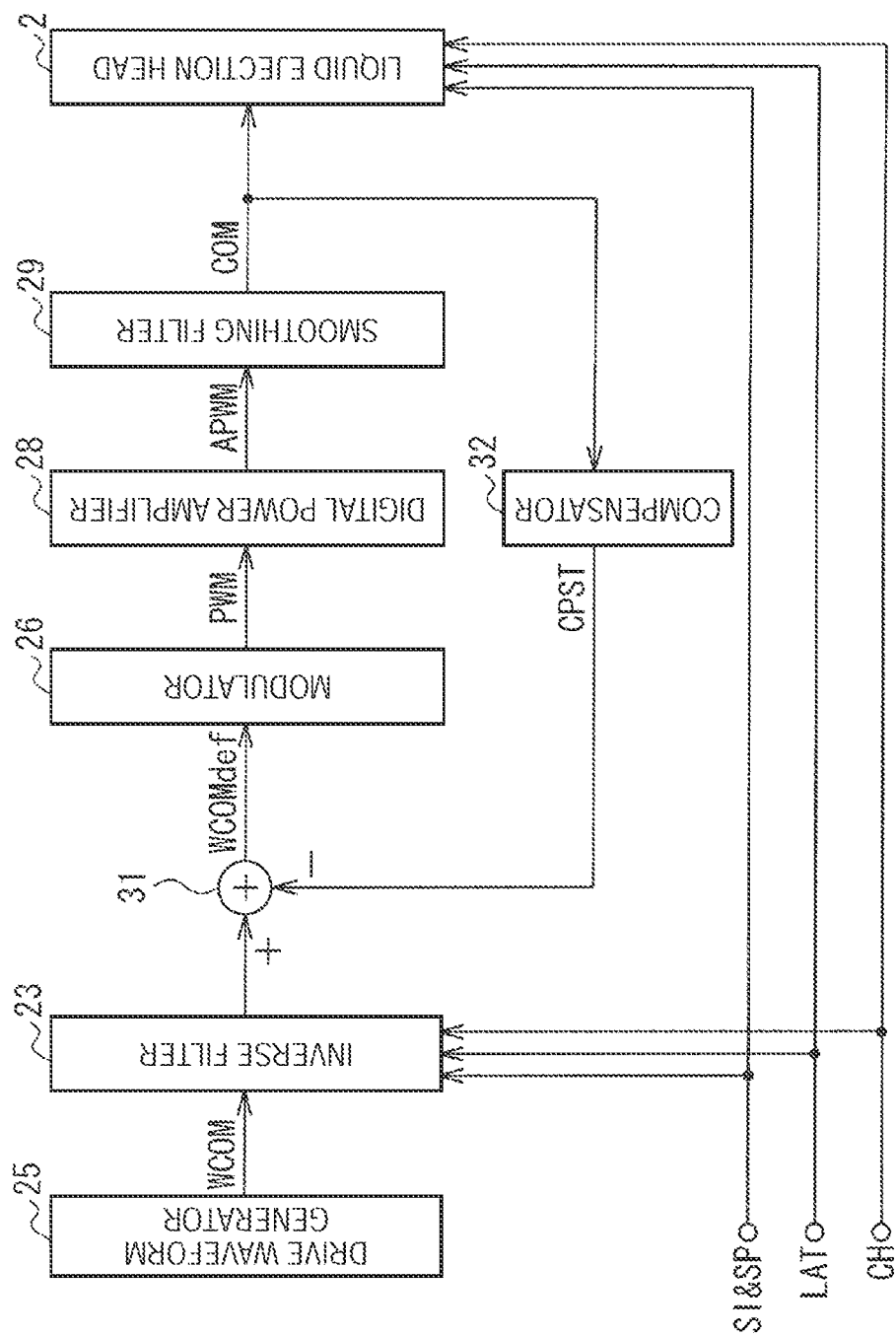
FIG. 14 is a block diagram of an actuator drive circuit showing a second embodiment of the liquid ejection printer using the liquid ejection device of the invention.

In the actuator drive circuit of the first embodiment, a closed loop formed of the adder-subtractor 31, the modulator 26, the digital power amplifier 28, the Lowpass Filter 29 (actually, the capacitance of the actuator 22 formed of a capacitive load such as a piezoelectric element is connected in parallel with the capacitor C in the Lowpass Filter 29), and the compensator 32 is depicted as shown in FIG. 12. Let the gain and the transfer characteristic of a drive signal output system formed of the modulator 26, the digital power amplifier 28, and the Lowpass Filter 29 (including the capacitance of the actuator 22 which is driven) be A and H, respectively. Then, the above-mentioned frequency characteristic with resonance is expressed as AH as shown in FIG. 13. On the other hand, let the transfer characteristic of the compensator 32 be β. Then, the transfer characteristic G of the closed loop shown in FIG. 12 is expressed in the following formula (1).

$$G(f_0) = \frac{A \cdot H(f_0)}{1 + A \cdot H(f_0) \cdot \beta(f_0)} = \frac{1}{\beta(f_0) + \frac{1}{A \cdot H(f_0)}} \quad (1)$$

Therefore, it is necessary simply to set the transfer characteristic β of the compensator 32 so that the transfer characteristic G of the closed loop is constant until a predetermined attenuation start frequency as shown by the chain double-dashed line in FIG. 13. Specifically, since, for example, $1/(A \cdot H)$ in formula (1) is shown by the broken line in the drawing, when $\beta + 1/(A \cdot H)$ becomes like the alternate long and short line in the drawing by setting the transfer characteristic β of the compensator 32 as shown by the solid line, the transfer characteristic G of the closed loop can be set as shown by the chain double-dashed line. As mentioned above, power loss occurs due to the current flowing through the resistor R of the compensator 32. However, it is possible to reduce the current value by increasing the resistance value of the resistor R and reduce the power loss.

As described above, in the liquid ejection device of the first embodiment, when a drive waveform signal WCOM is generated by the drive waveform generator 25, pulse modulation is performed on the signal from the drive waveform generator 25 by the modulator 26, power amplification is performed on the modulated signal PWM by the digital power amplifier 28, and the amplified digital signal APWM is smoothed by the Lowpass Filter 29 to obtain a drive signal COM (a drive pulse PCOM) of the actuator 22, the phase of the drive signal COM (the drive pulse PCOM) is advanced by the compensator 32 to obtain a negative feedback signal CPST, and the adder-subtractor 31 which is a subtractor inputs a differential signal WCOMdef between the drive waveform signal WCOM and the negative feedback signal CPST to the modulator 26 as an input signal. As a result, it is possible to compensate for the resonance characteristic produced when no damping resistor is used in the Lowpass Filter 29 by using the negative feedback signal CPST. This eliminates the need for a damping resistor and reduce power loss.

Next, a second embodiment of the liquid ejection device of the invention will be described. As in the case with the first embodiment described above, the liquid ejection device of this embodiment is a liquid ejection device applied to a liquid ejection printer, and a schematic configuration, an area near a liquid ejection head, a control device, a drive signal, and a switching controller are the same as those in the first embodiment. Therefore, in the following description, such components as are similar to those in the first embodiment are identified with the same reference numerals and signs, and the explanations thereof will be omitted. In the second embodiment, an inverse filter 23 is provided between the drive waveform generator 25 and the adder-subtractor 31. The inverse filter 23 includes a control unit, and can control its own frequency characteristic according to the number of actuators 22 which are driven. As is well known, the inverse filter 23 can be configured by computing performed by a program product. Therefore, the inverse filter 23 including the control unit can also be configured in the control unit 62 in the control circuit described above. That is, all the component elements from the drive waveform generator 25 to the modulator 26 can be digitized.

Figure 15:
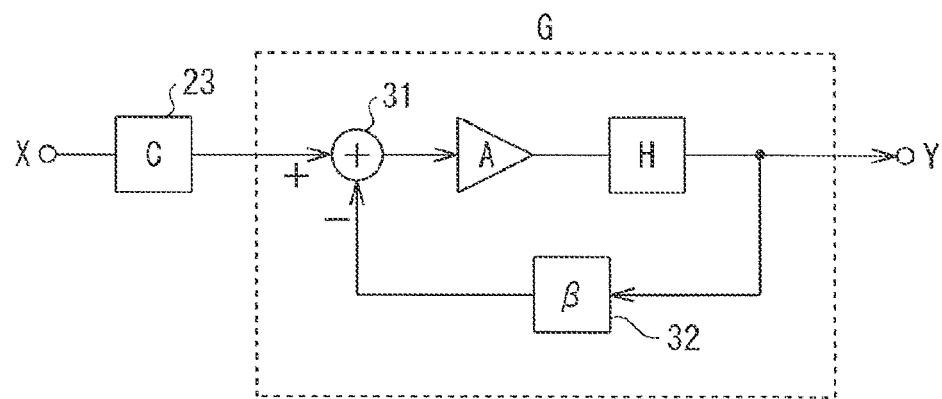
FIG. 15 is an explanatory diagram of a closed loop in the actuator drive circuit of FIG. 14.

In the actuator drive circuit in the second embodiment, a closed loop formed of the adder-subtractor 31, the modulator 26, the digital power amplifier 28, the Lowpass Filter 29, the capacitance of the actuator 22, and the compensator 32 is shown in FIG. 15. The transfer characteristic of the inverse filter 23 is assumed to be C. The transfer characteristic G0 of the whole system including the inverse filter 23 is expressed in the following formula (2).

$$C(f_0) \cdot G(f_0, N) = C(f_0) \frac{A \cdot H(f_0, N)}{1 + A \cdot H(f_0, N) \cdot \beta(f_0)} \quad (2)$$
$$= G0$$

Figure 16:
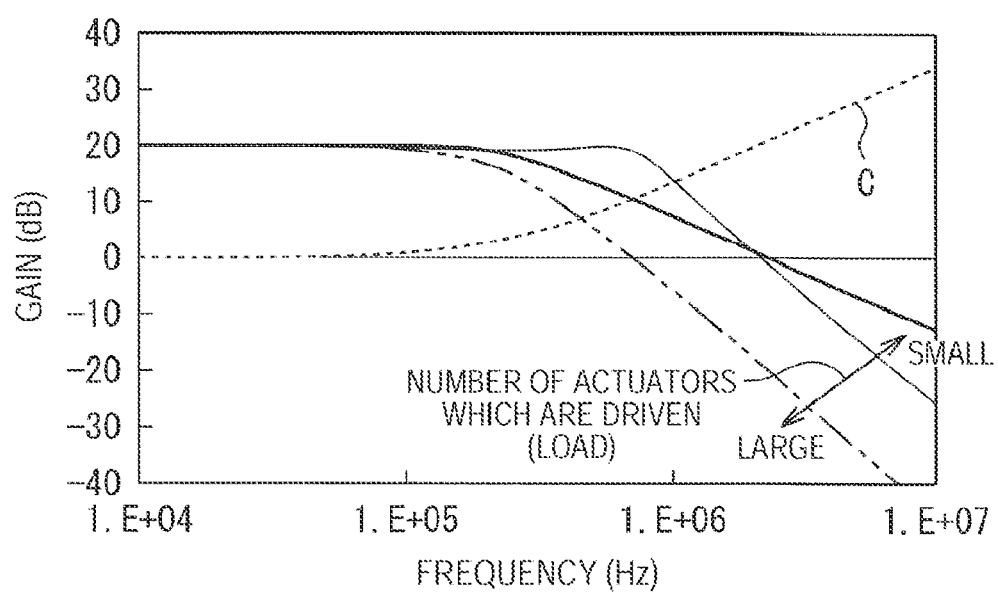
FIG. 16 is an explanatory diagram of a correction of the frequency characteristic of the closed loop, the correction made by an inverse filter.

As described in WO 2007/083669, for example, when the number of actuators 22 which are driven changes, the frequency characteristic of the closed loop changes. The feature is shown in FIG. 16. In this case, as mentioned above, since the resonance of the closed loop is suppressed by the negative feedback signal CPST from the compensator 32, the frequency characteristic changes as the attenuation start frequency changes, and the larger the number of actuators 22 which are driven is (the heavier the load is), the lower the attenuation start frequency becomes.

Therefore, as the characteristic of the inverse filter 23, as shown by the broken line in FIG. 16, it is necessary simply to increase the attenuation start frequency when the number of actuators 22 is large (the load is heavy) by using a so-called high-pass filter by which a high frequency band is emphasized. The number of actuators 22 which are driven can be determined based on the drive pulse selection data SI&SP. Thus, when the inverse filter 23 is a high-pass filter, for example, by controlling the gain of the high-pass filter according to the number of actuators 22 which are driven, it is possible to make the gain of the closed loop constant in a predetermined frequency domain. As a result, an attenuation start frequency required for the Lowpass Filter 29 can be maintained constant.

As described above, in the liquid ejection device of the second embodiment, by correcting the frequency characteristic of the closed loop formed of the modulator 26, the digital power amplifier 28, the Lowpass Filter 29, the capacitance of the actuator 22, and the compensator 32, the frequency characteristic which changes with the number of actuators 22 which are driven, so as to be constant in a predetermined frequency domain by the inverse filter 23, it is possible to ensure the accuracy of the drive signal.

In the embodiments described above, only a case in which the liquid ejection device of the invention is applied to a line head liquid ejection printer has been described in detail; however, the liquid ejection device of the invention can also be applied similarly to a multipath liquid ejection printer.

The liquid ejection device of the invention can also be embodied as a liquid ejection device that ejects any liquid (including not only a liquid, but also a liquid substance in which particles of functional material are dispersed and a fluid substance such as gel) other than ink and a fluid other than a liquid (such as a solid that can be ejected as a fluid). For example, the liquid ejection device of the invention may be a liquid ejection device that ejects a liquid substance containing dispersed or dissolved material such as electrode material or color material which is used in the production of a liquid crystal display, an EL (electroluminescence) display, a surface emitting display, and a color filter, a liquid ejection device that ejects a bioorganic substance used in the production of a biochip, and a liquid ejection device that is used as a precision pipette and ejects a liquid used as a sample. Furthermore, the liquid ejection device of the invention may be a liquid ejection device that ejects lubricating oil to a precision instrument such as a clock and a camera at a proper point with a high degree of accuracy, a liquid ejection device that ejects, to a substrate, a transparent resin liquid such as ultraviolet curable resin for forming a micro hemispherical lens (an optical lens) or the like used in an optical communication element etc., a liquid ejection device that ejects an etching liquid such as an acid or alkali for etching a substrate etc., a fluid substance ejection device that ejects gel, and a fluid ejection recording apparatus that ejects a solid such as powder like toner. Moreover, the liquid ejection device of the invention may be a liquid ejection device used as a surgical instrument that incises or excises a living tissue by ejecting a liquid such as water or a salt solution in pulses. The invention can be applied to any one of these ejection devices.

This application claims priority to Japanese Patent Application No. 2009-257375, filed on Nov. 10, 2009, the entirety of which is hereby incorporated by reference.

What is claimed is:

1. A liquid ejection device comprising:
a drive waveform generator generating a drive waveform signal;

a modulator performing pulse modulation on a signal from the drive waveform generator to provide a modulated signal;

a digital power amplifier performing power amplification on the modulated signal to provide an amplified digital signal;

a lowpass filter smoothing the amplified digital signal to provide a drive signal of an actuator;

a compensator advancing a phase of the drive signal to provide a negative feedback signal; and a subtractor providing a differential signal between the drive waveform signal and the negative feedback signal as an input signal to be inputted to the modulator.

2. The liquid ejection device according to claim 1, further comprising:

an inverse filter provided between the drive waveform generator and the subtractor and correcting the frequency characteristic of a closed loop formed of the modulator, the digital power amplifier, the lowpass filter, the capacitance of the actuator, and the compensator so as to be constant in a predetermined frequency domain.

3. A liquid ejection printer comprising the liquid ejection device according to claim 1.

\* \* \* \* \*